United States Patent
Simmons, Jr.

(10) Patent No.: US 10,016,256 B2
(45) Date of Patent: Jul. 10, 2018

(54) METHODS AND APPARATUS FOR PREPARING A DENTAL IMPLANT SITE

(71) Applicant: Earl Wayne Simmons, Jr., San Antonio, TX (US)

(72) Inventor: Earl Wayne Simmons, Jr., San Antonio, TX (US)

(*) Notice: Subject to any disclaimer, the term of this patent is extended or adjusted under 35 U.S.C. 154(b) by 695 days.

(21) Appl. No.: 14/601,032

(22) Filed: Jan. 20, 2015

(65) Prior Publication Data
US 2015/0250557 A1   Sep. 10, 2015

Related U.S. Application Data

(60) Provisional application No. 61/949,908, filed on Mar. 7, 2014.

(51) Int. Cl.
| A61C 3/03 | (2006.01) |
| A61C 1/08 | (2006.01) |
| A61C 8/00 | (2006.01) |
| A61C 1/18 | (2006.01) |

(52) U.S. Cl.
CPC .............. *A61C 3/03* (2013.01); *A61C 1/084* (2013.01); *A61C 8/0089* (2013.01); *A61C 1/18* (2013.01)

(58) Field of Classification Search
CPC ... A61B 17/16; A61B 17/162–17/1631; A61B 17/1659; A61B 17/1673; A61C 1/082; A61C 1/084
USPC ............. 606/79, 80, 84, 85; 433/165, 166
See application file for complete search history.

(56) References Cited

U.S. PATENT DOCUMENTS

| 2,807,264 A * | 9/1957 | Tuck .................. A61B 17/1673 433/166 |
| 3,894,339 A * | 7/1975 | Manzi ...................... A61C 3/02 433/166 |
| 5,277,583 A * | 1/1994 | Chalifoux .............. A61C 13/30 433/220 |
| 5,362,237 A * | 11/1994 | Chalifoux .............. A61C 13/30 433/220 |
| 5,782,636 A * | 7/1998 | Armstrong ........... A61C 8/0089 408/209 |
| 6,186,788 B1 * | 2/2001 | Massad .................... A61C 3/02 433/165 |
| 6,565,356 B2 * | 5/2003 | Oyamada ................. A61C 3/02 433/165 |
| 6,682,349 B1 * | 1/2004 | Logeart .................... A61C 3/02 408/226 |
| RE38,630 E * | 10/2004 | Lazzara ............... A61C 8/0089 433/165 |
| 7,094,055 B2 * | 8/2006 | Senia ....................... A61C 5/42 433/102 |
| 8,273,088 B2 * | 9/2012 | Zalenski ............ A61B 17/1659 606/279 |

(Continued)

OTHER PUBLICATIONS

Meisinger Dental Catalogue 2015/16. p. 252, Figs. 508G and 508F (attached). http://www.meisinger.de/index.php/dental-catalogue.html.

*Primary Examiner* — Eric S Gibson

(57) ABSTRACT

A dental implant site preparation tool (10) includes a shaft (12) and a working end (14). The working end includes a cutting surface (16) that includes cutting features. The working end (14) also includes a substantially smooth tip (18) that may have a convex shape. A method of preparing a dental implant site includes working the tool (10) so as to create a shape that matches that of an implant.

11 Claims, 7 Drawing Sheets

(56) References Cited

U.S. PATENT DOCUMENTS

| | | | | |
|---|---|---|---|---|
| 8,998,611 B2* | 4/2015 | Yazigi | A61C 1/084 | |
| | | | 433/165 | |
| 9,198,743 B2* | 12/2015 | Wang | A61C 8/0089 | |
| 9,707,051 B1* | 7/2017 | Livernois | A61C 3/02 | |
| 2002/0107521 A1* | 8/2002 | Petersen | A61B 17/1615 | |
| | | | 606/85 | |
| 2003/0083681 A1* | 5/2003 | Moutafis | A61B 17/1617 | |
| | | | 606/167 | |
| 2005/0003327 A1* | 1/2005 | Elian | A61C 8/0089 | |
| | | | 433/165 | |
| 2006/0100632 A1* | 5/2006 | Fell | A61B 17/1659 | |
| | | | 606/81 | |
| 2006/0188843 A1* | 8/2006 | Furney | A61D 5/00 | |
| | | | 433/166 | |
| 2010/0094297 A1* | 4/2010 | Parmigiani | A61B 17/1673 | |
| | | | 606/80 | |
| 2010/0121330 A1* | 5/2010 | Parmigiani | A61B 17/1617 | |
| | | | 606/79 | |
| 2013/0011810 A1* | 1/2013 | Cho | A61C 8/0089 | |
| | | | 433/165 | |
| 2014/0243830 A1* | 8/2014 | Baptist | A61B 17/16 | |
| | | | 606/80 | |
| 2015/0250557 A1* | 9/2015 | Simmons, Jr. | A61C 3/03 | |
| | | | 433/118 | |

* cited by examiner

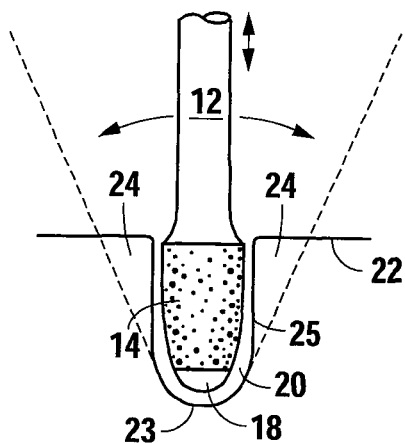
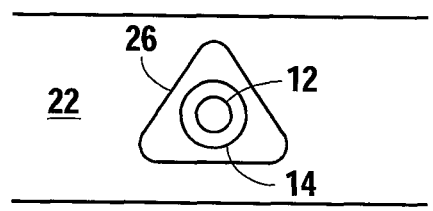
Fig. 2        Fig. 3
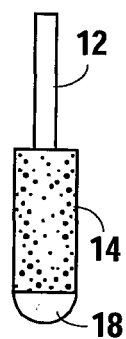  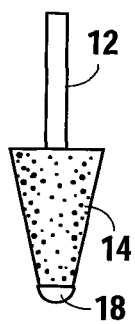  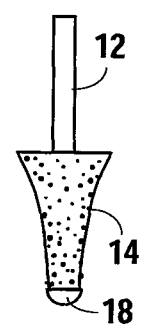
Fig. 4        Fig. 5        Fig. 6
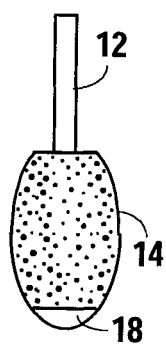   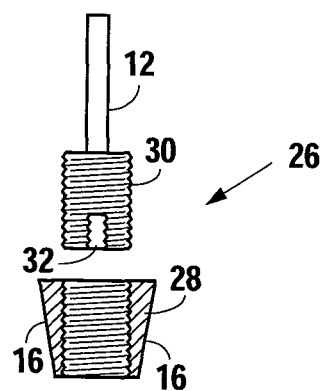
Fig. 7        Fig. 8

METHODS AND APPARATUS FOR PREPARING A DENTAL IMPLANT SITE

CROSS-REFERENCE TO RELATED APPLICATION AND PRIORITY INFORMATION

This application claims the benefit of prior filed U.S. provisional application No. 61/949,908, entitled "Eccentric Dental Implant System and Toggle Burr", filed Mar. 7, 2014.

TECHNICAL FIELD OF THE INVENTION

This invention relates generally to dentistry, and more particularly to methods and apparatus for preparing a dental implant site.

BACKGROUND OF THE INVENTION

In recent years, the use of dental implants has become widespread. Concentrically shaped implants are the most common, and offer relatively easy installation. Their round shape allows the use of conventional drills and screwing techniques. However, well known functional, hygienic, and aesthetic problems can be associated with concentric implants.

Eccentrically shaped implants, which more closely match natural teeth shapes, may reduce such problems. However, eccentric implants are often more difficult to install than concentric implants, partly due to the difficulty of preparing eccentric osteotomies, which sometimes require special instrumentation. For example, some eccentric implants employ an eccentric base, which must be implanted into a prepared site in the jawbone. Improper preparation of the site can lead to significant problems.

In particular, if the implant site is not properly prepared, the implant may not integrate with the jawbone with sufficient strength to provide adequate stability. As examples of poor implant sites, the site may be too large, or too deep, or too shallow, or too tapered, or mismatched to the shape of the implant, leading to voids or insufficient jawbone-to-implant surface contact, or to hygienic or aesthetic problems. Relatedly, if the implant site is too deep or too tapered, there may be insufficient bone mass available for adequately securing an implant anchor.

Therefore, a need has arisen for improved methods and apparatus for preparing dental implant sites.

SUMMARY OF THE INVENTION

In accordance with the teachings of the present invention, methods and apparatus for preparing dental implant sites are provided that eliminate or substantially reduce problems associated with prior art systems.

In a particular embodiment, an apparatus for preparing a dental implant site in a jawbone is provided which comprises an osteotomy seat having a working surface and a burr having a shaft with a working end. The working end comprises a cutting surface and a smooth tip for contact with the working surface.

Also provided is a method of preparing a dental implant site in a jawbone, which includes forming an osteotomy site in a bone, the site having a bottom and sidewalls, placing an osteotomy seat on the bottom of the osteotomy, and working a burr upon the osteotomy seat to widen the osteotomy site by cutting the sidewalls.

Working may include toggling the burr, vibrating the burr, rotating the burr, reciprocating the burr, or any combination of one or more of these motions.

Also provided is an instrument for preparing a dental implant site in a jawbone that comprises a shaft having a working end. The working end comprises a cutting surface and a smooth tip. A vibrational source is coupled to the shaft.

Also provided is an instrument for preparing a dental implant site in a jawbone that comprises a shaft having a working end. The working end includes a cutting surface and a smooth tip, wherein the smooth tip is broad enough so as to prevent the creation of excessive depressions in the jawbone when the smooth tip is in forced contact with the jawbone.

In another embodiment, an instrument for preparing a dental implant site in a jawbone is provided which comprises a shaft having a working end with a cutting surface. A pivot member is coupled to the working end, and an extension is engaged with the pivot member, such that the working end pivots on the extension.

An important technical advantage of the invention is that it provides for predictably accurate eccentric preparation of the bone. In particular, the smooth tip of the burr prevents cutting the bottom of the osteotomy site, thereby preventing any substantial damage or alteration of the bottom of the site. This helps ensure that, among other things, sufficient jawbone exists for stable anchoring of an implant. Also, the osteotomy seat and extensions provide a stable platform on which a burr can be worked, and isolates the bottom of the osteotomy site from direct contact with the burr to further prevent damage to the bottom of the osteotomy site. Also, by coupling the burr to a vibrational source, very accurate site widening can be achieved.

BRIEF DESCRIPTION OF THE DRAWINGS

Reference is made in the description to the following briefly described drawings, which are not drawn to scale, with certain features enlarged for clarity, in which like reference numerals indicate like features:

FIGS. 2 and 3 illustrate use of a burr according to the teachings of the present invention;

FIGS. 4-7 illustrate front views of various embodiments of burrs according to the teachings of the present invention;

FIG. 8 is a cross-sectional view of another embodiment of a burr according to the teachings of the present invention;

DETAILED DESCRIPTION OF THE INVENTION

Figure 1:
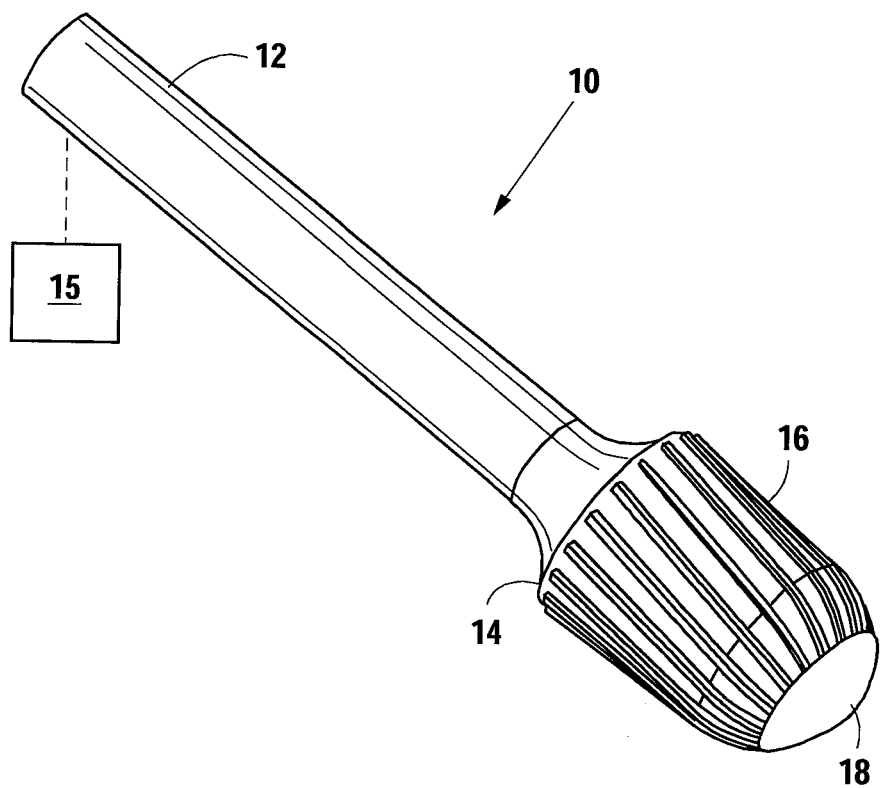
FIG. 1 is a schematic perspective diagram of a burr according to the teachings of the present invention.

As shown in FIG. 1, burr 10 includes a shaft 12 and a working end 14. Shaft 12 may include a latch (or any other suitable attachment feature, such as, without limitation, a threaded male/female joint) for coupling to and uncoupling from a tool (shown schematically as reference 15) that rotates and/or toggles and/or vibrates the burr. For example, and without limitation, the shaft may be coupled to a drill for rotation, or to any suitable vibration generator (such as a piezoelectric or ultrasound unit). Also, the burr 10 may be hand-manipulated without a tool. In such a case, the shaft 12 may be attached to a hand piece, or sized for use with a surgeon's hand, and may include grip features. Shaft 12 may be any suitable shape in cross section, whether round or eccentric.

The working end 14 includes cutting surface 16, and a substantially smooth tip 18. Cutting surface 16 does not extent to the smooth tip 18. In use, working of the burr results in the cutting surface 16 cutting into the jawbone to widen the osteotomy site (substantially laterally) in order to create the desired shape of the eccentric implant site. The smooth tip 18, because it is not a cutting surface, will not cause any substantial deepening or broadening of the site while the burr is worked to widen the site. Thus, the smooth tip 18 helps ensure that, among other things, sufficient jawbone exists for stable anchoring of an implant.

Preferably, the widest cross section of the burr is no broader than the minimum outside dimension of the implant for which the osteotomy site is being prepared. For example, if the plan view of the implant is oval (thus there is a minimum and a maximum outside diameter), the burr is preferably no broader than the minimum diameter. Furthermore, the smooth tip 18 is preferably rounded, but may be flat. Also, to minimize damage to the bottom of the osteotomy site, it is it is preferred that the tip 18 be relatively broad, and not protrude in a narrow point that could puncture or create depressions in the bottom of the site when the burr is in forced contact with the site (i.e., while the burr is worked).

Any suitable heights (with the long axis of the shaft being considered vertical) for the cutting surface 16 and the tip 18 may be chosen, as appropriate for the application.

As an example of one particular use of the burr 10, which is shown in FIG. 2, the working end 14 is inserted into a primary implant osteotomy (hole or site) 20 that has been formed in bone 22. For general reference, the site 20 is considered to have a bottom 23 and sidewalls 25. The burr 10 is then worked (by rotation, reciprocation, vibration, and/or toggling (and/or any other suitable motion)), and the cutting surface 16 cuts into bone sections 24 of bone 22 to create the desired (often eccentric) shape for receiving the implant. Because the tip 18 of the burr 10 is smooth, the tip 18 will not cut or substantially deepen or broaden the primary implant osteotomy site 20.

As shown in FIG. 3 (a top view of FIG. 2), as the burr 10 is worked, sections 24 of bone 22 are cut away to form whatever shaped is desired, whether concentric or eccentric, to accommodate various implant patterns. The particular shape shown in FIG. 3 is a soft triangular shape. In this way, the site is prepared to match the shape of any implant, including eccentrically shaped implants.

The working end 14 may be formed of any suitable material, including, without limitation, any surgical metal or ceramic, and the cutting surface 16 may include any suitable cutting features and patterns. Also, the cutting surface may comprise diamond (or other material) grit of any appropriate coarseness or any suitable roughened surface. The smooth tip 18 may be of any suitable material, including, without limitation, any surgical metal, nylon, or an appropriate ceramic material (which may reduce friction and heat), and have any suitable surface contour, preferably convex.

FIGS. 4-7 illustrate particular examples for the working end 14. FIG. 4 shows a cylindrical working end 14, with stippling used to indicate cutting surface 16 (as discussed above, any suitable cutting surface may be used). FIG. 5 illustrates a conical working end 14. FIG. 6 illustrates a working end 14 having a concave contour, and FIG. 7 illustrates a working end 14 with a convex contour. These are particular examples, and any suitable shape and surface may be used.

The smooth tip 18 may be integral with the working end 14. Alternatively, the smooth tip 18 may be an attachment that is coupled to the working end 14. Attachment may be made in any suitable way. For example, and without limitation, attachment may be via a snap fit or through threaded engagement, or may be via a ball-bearing fitment or other suitable mechanism so that the tip 18 does not necessarily rotate with the cutting surface 16.

The working end 14 may be formed integrally with the shaft 12, or may be attached to the shaft 12, for example (and without limitation) by threaded engagement. As shown in FIG. 8, which is a cross sectional view of an unassembled toggle burr 26, the working end 14 may be formed by attaching a sleeve 28 to end 30. Sleeve 28 and end 30 may be threaded to allow their coupling. Sleeve 28 may have any desired shape, as discussed above in connection with FIGS. 4-7, and includes the cutting surface 16. The diameter of end 30 may be less than, equal to, or greater than that of shaft 12 above the end 30. In the example shown, the diameter of end 30 is greater than that of shaft 12. End 30 may be formed integrally with shaft 12 or attached by any suitable technique.

Also shown in FIG. 8 is a threaded bore 32, which may be used to attach smooth tip 18. However, no such bore is required because tip 18 may be formed integrally with or otherwise attached to the burr or the working end 14 or the sleeve 28.

Whether integral or attached, the tip 18 may be elongated, or include an extension, to allow lateral cutting to be maintained at a desired vertical distance from the bottom of the osteotomy, helping to maximize available bone depth for anchoring of the implant. In one embodiment, the attachable tip 18 may be disposable.

Furthermore, a surgical guide stop or stent (which may be a hollow cylinder or cone, a plate, or any suitable boundary) may be placed over or adjacent the implant site to limit the movement of the burr 10, thereby limiting lateral cutting and the size of the osteotomy.

Burrs according to the present invention may be placed directly into an osteotomy site to form the desired shape. However, another aspect of the current invention is an osteotomy seat upon which the burr is worked.

Figure 9:
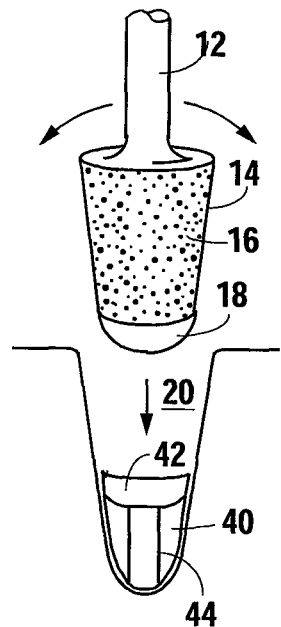
FIG. 9 illustrates a perspective view of a toggle burr and osteotomy seat according to the teachings of the present invention.

As shown in FIG. 9, an osteotomy seat 40 is placed into the bottom of the primary osteotomy site 20. Osteotomy seat 40 may have any desired height (to facilitate surface 16 cutting bone at the desired vertical distance from the bottom of the site 20), and its diameter (although seat 40 need not be cylindrical) should be selected to snugly fit into the bottom of the site 20. Seat 40 may be solid or hollow, or partially solid or hollow. The seat 40 includes a working surface 42 (in the illustrated embodiment surface 42 is concave hemispherical) that is contacted by tip 18 of a burr as the burr is worked. Surface 42 is preferably smooth. Also, the seat 40 may include anti-rotation features on its sidewalls, such as ribs 44. Seat 40 may be made of any suitable material, including, without limitation, surgically suitable metals, nylons, and ceramics.

In operation, the seat 40 acts as a stop upon which (at surface 42) the burr is rotated, toggled, vibrated, or otherwise worked, thereby shielding the deep architecture of the osteotomy from inadvertent damage from direct motion of the burr. Although the embodiment of FIG. 9 shows a concave surface 42 for contact with a convex surface of tip 18, in an alternate arrangement the tip 18 may be concave, and the surface 42 convex. Indeed any suitable contour or shape may be used.

Figure 10:
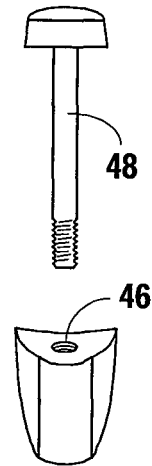
FIG. 10 illustrates a perspective view of an insertion and removal tool for an osteotomy seat according to the teachings of the present invention.

A threaded bore 46 may be provided through surface 42 to assist in placement and removal of the seat 40. In particular, as shown in FIG. 10, a threaded tool 48 is inserted into the bore 46 during insertion and removal to place and remove the seat 40. The tool 48 is unscrewed, and the seat 40 left at the bottom of the site 20, while the toggle burr is used to form the implant site. Although threads are illustrated, any suitable mechanism or feature may be used to facilitate engagement of the seat 40 with an insertion/removal tool. As a non-limiting example, surface 42 may include one or more raised handle features that facilitate removal or insertion with a forceps.

Figure 11:
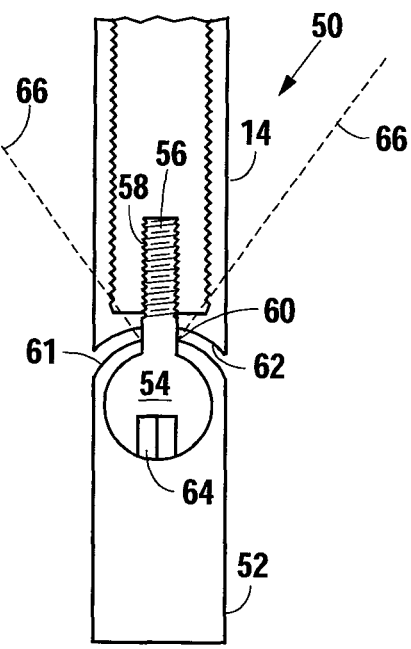
FIG. 11 illustrates another embodiment of a burr according to the teachings of the present invention.
Figure 12:
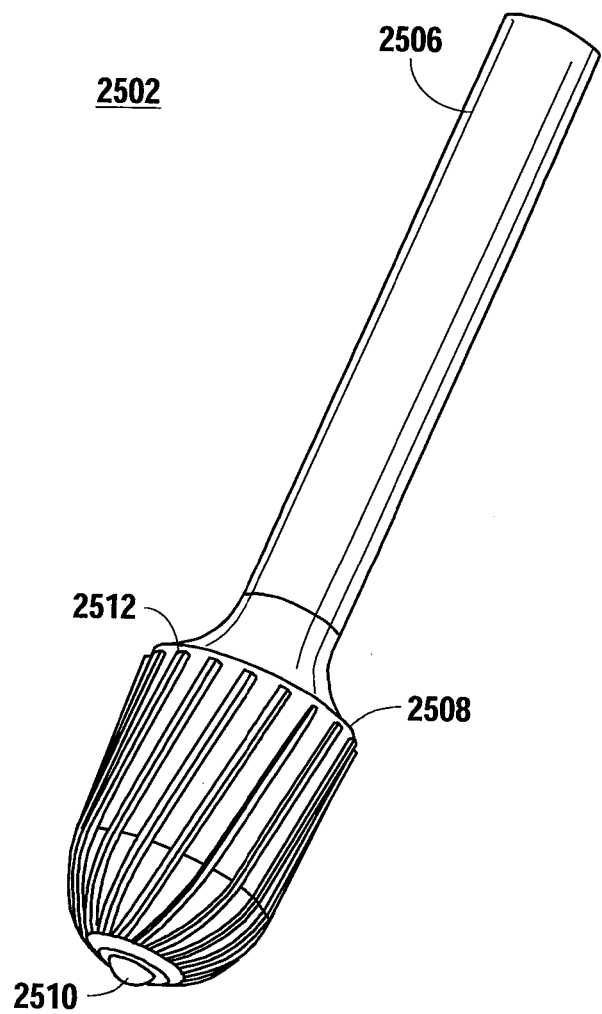
FIGS. 12-15 illustrate details of the burr of FIG. 1.
Figure 13:
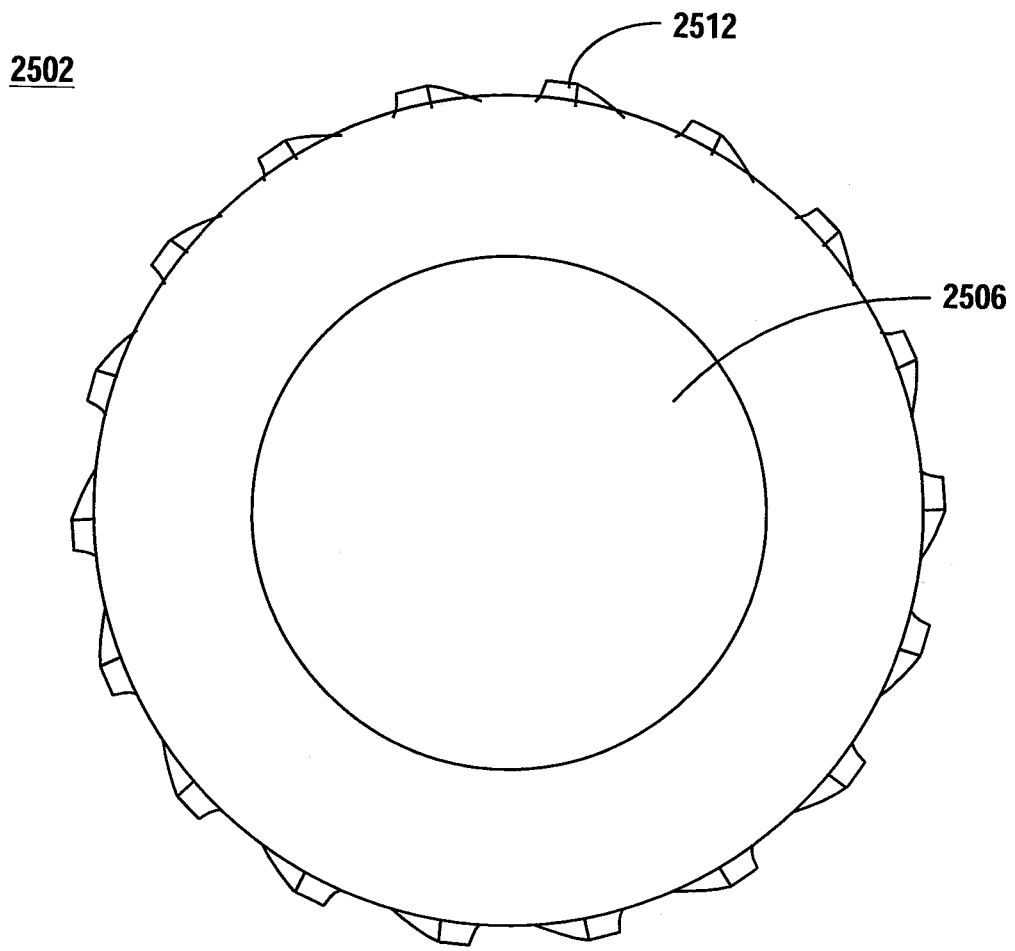
Figure 14:
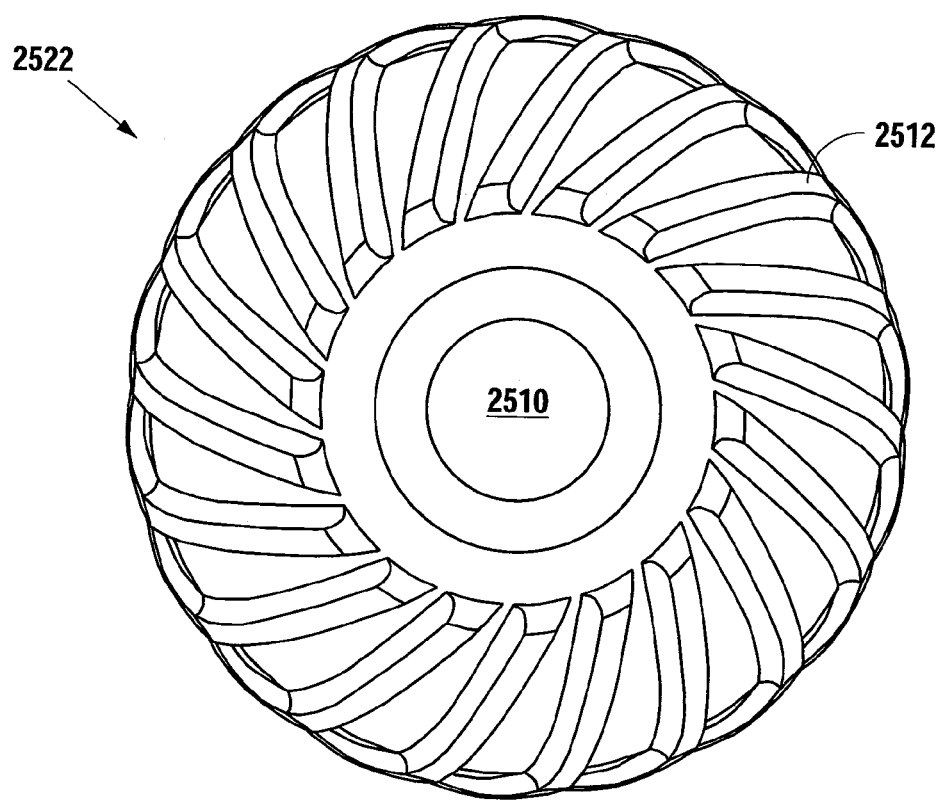

Another embodiment is shown in cross sectional FIG. 11, in which the working end 14 of a burr is coupled to an extension 52 and pivot member 54 (which is a sphere in the illustrated example). Sphere 54 includes an attachment member 56 for attachment to the burr 50 at working end 14. In the particular example shown, attachment member 56 is a threaded shaft, for engagement with a matching threaded bore 58 in burr 50. Extension 52 is a hollow shaft with an opening 60 at its burr end through which attachment member 56 passes. Extension 52 is preferably convex at its burr end 61 (although any suitable contour may be used) and engages with surface 62 (which may be concave or any suitable contour). Sphere 54 may include an internal hexagonal head recess 64 for receiving a hexagonal driving tool for attachment and disengagement from the burr.

In operation of the embodiment of FIG. 11, the extension 52 acts as an extended tip or a stop to the burr 50 (surface 62 engaging with surface 61), and pivot member 54 allows the burr to pivot on the extension 52. In the example shown, sphere 54 can rotate freely about it vertical axis, but is constrained in its rotation about horizontal axes by the size of hole 60. Thus, a drilling motion will not be limited, but toggling will be limited by the size of the hole 60, as depicted in FIG. 11 by the dashed borderlines 66. The height of extension 52 is selected to facilitate surface 16 cutting bone at the desired vertical distance from the bottom of the osteotomy site, and its diameter (although it need not be cylindrical) should be selected to snugly fit into the bottom of the site.

Although the embodiment of FIG. 11 shows a ball and socket arrangement of sorts, any suitable arrangement could be used to facilitate toggling and engagement of surfaces 61 and 62, such as a nylon connector cable, a stainless steel flexible cable, or a universal hinge joint.

Following are examples of various uses of embodiments of the burrs described herein.

When a cross-section of an edentulous site is presented in the patient, it is desired to minimize the bone removal toward the buccal or facial plate of bone in many instances. This occurs when there is a concave shape to the maxilla in the anterior esthetic zone. In this instance a concave implant embodiment, and thus the burr with a concave contoured surface 16 would be the desired embodiments. This will preserve bone thickness in the labial wall and allow for immediate grafting in the case of a fresh extraction socket. In many anterior maxillary incisors, the labial wall is very thin and can easily be perforated or damaged. This approach allows toggling without destroying the labial wall of the bone.

In the mandibular incisor area, the teeth are so narrow and the facial/lingual dimension double the mesial distal dimension, that this requires a very narrow diameter primary osteotomy and then a narrow burr, with a concave contour to preserve the mesial distal intraradicular bone. This will also aid in prevention of nicking an adjacent root while drilling.

In the maxillary incisor area, the teeth in cross-section are soft triangulated and the burr can be worked to create an osteotomy that accommodates this shape. A try-in of the implant will quickly identify areas where bone needs to be removed and the burr reinserted to accomplish this.

In the molar region, the burr may have a more definite convexity to the wall when required. The implant design will dictate the preferred burr shape. Often models will be available for many shapes based on osseous morphology identified in the CT scans.

In practice, a kit of burrs having various sizes and shapes (including variously shaped attachable tips or sleeves for the attachable embodiments and variously shaped osteotomy seats) will be provided for flexibility in best preparing sites for different implants.

For completeness, the following two paragraphs are copied from the provisional application of which this present application claims benefit (co-pending, prior filed U.S. provisional application No. 61/949,908, entitled "Eccentric Dental Implant System and Toggle Burr", filed Mar. 7, 2014). The only difference is that the original FIGS. 25-28 have been renumbered to FIGS. 12-15. Base member 108 referred to below corresponds to an implant base.

Figure 15:
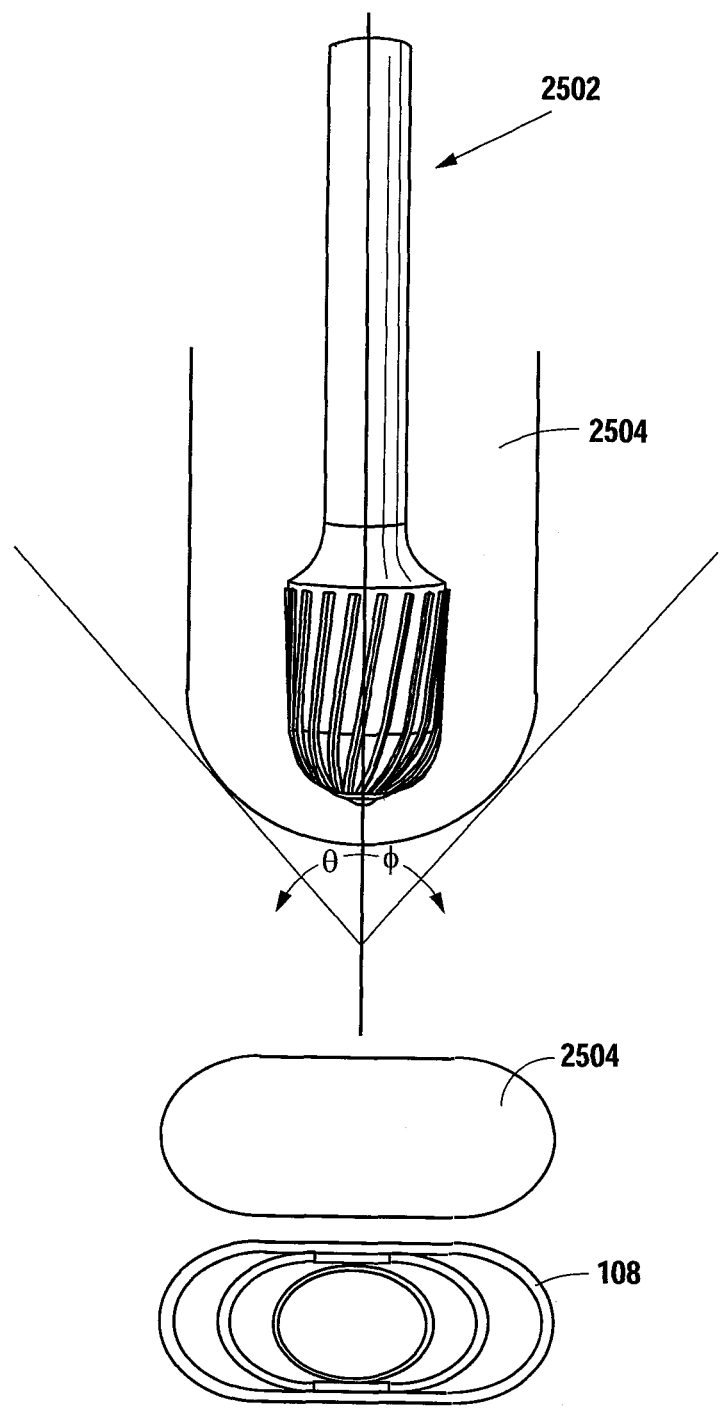

Referring now to FIGS. 12-15, an example burr 2502 is shown in accordance with the principles of the present disclosure. In general, the burr 2502 may be coupled to a tool (not shown) that rotates the burr to shape features into bone, such as an osteotomy cavity 2504 as shown in top-down view in FIG. 15. Here, the shape of the osteotomy cavity 2504 generally corresponds to the shape of the base member 108 (also shown in top-down view in FIG. 15). In the present example, the burr 2502 includes a post 2506 terminated by a bulbous end 2508. The bulbous end 2508 is formed to include a grinding tip 2510 along with a plurality of grinding ridges 2512 that are defined in a particular pattern or pitch. In one example, the burr 2502 may be coupled to a tool in a manner so that the tool may be held stationary while the burr 2502 is actuated or toggled through a particular angular range of motion as shown in FIG. 15.

In use, a pilot hole will first be drilled or cored to form a generally cylindrical opening or recess in the jawbone. Burr 2502 is placed within the opening. Typically, the outer diameter of burr 2502 will generally correspond to the cylindrical opening. Burr 2502 is rotated while also being toggled with a desired motion. The angular motion of the burr 2502 may be controlled to sweep through or around to any angle as desired to carve or otherwise define the osteotomy cavity 2504. Additionally, or alternatively, the burr 2502 may be held in place at an angle as shown in FIG. 15, whereby the tool itself may be manipulated though any desired range of motion to shape features into bone, similar to conventional tools used to shape features in to bone. Advantageously, the round/curved shape of the bulbous end 2508 may permit the apical end of the osteotomy to remain round and centered no matter what pattern one would rock the toggle at the coronal (top) of the bone (e.g., oval, rectangle, triangle, etc.). That makes it very easy to match an aligned through-hole that the implant passes through. In some embodiments, the burr 2502 may be formed of stainless steel material. Other embodiments are possible. In some embodiments, dimensions of the burr 2502 may be in a range from about 2.0 mm to about 8.0 mm in diameter inclusive, and various lengths to allow access in the mouth.

The particular embodiments and descriptions provided herein are illustrative examples only, and features and advantages of each example may be interchanged with, or added to the features and advantages in the other embodiments and examples herein. Moreover, as examples, they are meant to be without limitation as to other possible embodiments, are not meant to limit the scope of the present invention to any particular described detail, and the scope of the invention is meant to be broader than any example. Also, the present invention has several aspects, as described above, and they may stand alone, or be combined with some or all of the other aspects.

And, in general, although the present invention has been described in detail, it should be understood that various changes, alterations, substitutions, additions and modifications can be made without departing from the intended scope of the invention, as defined in the following claims.

What is claimed is:

1. Apparatus for preparing a dental implant site in a jawbone, comprising:
    an osteotomy seat having a working surface;
    a burr having a shaft with a working end, wherein the working end comprises:
    a cutting surface; and
    a smooth tip adapted for unconnected contact with the working surface, such that the unconnected contact between the smooth tip and the working surface allows substantial lateral toggling of the burr.

2. The apparatus of claim 1, further comprising a vibrational source coupled to the shaft.

3. An instrument for preparing a dental implant site in a jawbone, comprising:
    a shaft having an integral working end with a cutting surface;
    a pivot member coupled to the working end; and
    an extension member adjacent the pivot member and separate from the shaft, the extension member having a hole through which the pivot member extends to couple to the working shaft, such that the working end pivots on the extension member.

4. The instrument of claim 3, wherein the pivot member has a rounded upper surface.

5. The instrument of claim 3, wherein the pivot member is substantially spherical.

6. The instrument of claim 3, wherein the extension member includes a first contoured surface, and the working end includes a second contoured surface, and wherein the first and second contoured surfaces matchingly engage, such that the working end pivots on the first contoured surface.

7. The instrument of claim 3, wherein the hole has a size, and the size of the hole limits a range of pivoting of the working end.

8. A method of preparing a dental implant site in a jawbone, comprising:
    forming an osteotomy site in a bone;
    placing an osteotomy seat in the osteotomy site, the osteotomy seat having a working surface;
    providing a burr having a shaft with a working end, wherein the working end comprises a cutting surface and a smooth tip;
    placing the smooth tip in unconnected contact with the working surface; and
    laterally toggling the burr upon the working surface to widen the osteotomy site.

9. The method of claim 8, further comprising vibrating the burr.

10. The method of claim 8, further comprising rotating the burr.

11. The method of claim 8, further comprising reciprocating the burr.

* * * * *